United States Patent [19]

Deutscher

[11] Patent Number: 4,982,481

[45] Date of Patent: Jan. 8, 1991

[54] EMBALMING DEVICE AND METHOD OF EMBALMING

[76] Inventor: George R. Deutscher, 12327 - St. Albert Trail, Edmonton, Alberta, Canada, T5L 4G9

[21] Appl. No.: 372,841

[22] Filed: Jun. 29, 1989

[51] Int. Cl.⁵ .............................................. A61G 17/00
[52] U.S. Cl. ........................................ 27/21.1; 27/23.1
[58] Field of Search .............................. 27/23.1, 28, 21

[56] References Cited

U.S. PATENT DOCUMENTS

| | | | |
|---|---|---|---|
| 300,989 | 6/1884 | Lovett | 27/23.1 |
| 416,223 | 12/1889 | Horsey | 27/23.1 |
| 4,780,940 | 11/1988 | Jay | 27/28 |

Primary Examiner—Richard E. Chilcot, Jr.
Attorney, Agent, or Firm—Anthony R. Lambert

[57] ABSTRACT

A disposable container is provided for storage of waste body fluids from the embalming process in a casket or coffin. The disposable container is tapered for the insertion into a coffin or casket and is vacuum tight for use during the aspiration process.

A system is also provided in which the disposable container is an essential part. The system includes a vacuum pump for evacuating the disposable container during aspiration, a trolley for supporting the disposable container during aspiration and a valve for directing body fluids from the embalming table into the disposable container.

A method of using the disposable container is also disclosed in which body fluids are drained into the disposable container, and the disposable container is placed in the casket or coffin for burial or cremation.

16 Claims, 4 Drawing Sheets

EMBALMING DEVICE AND METHOD OF EMBALMING

FIELD OF INVENTION

This invention relates to an apparatus and method of embalming, and particularly to the removal of body fluid during the embalming process and the disposal of the body fluid without contaminating the environment.

BACKGROUND OF THE INVENTION

During embalming, body fluids are removed from the body and replaced with chemical preservatives such as formalin. The process usually takes place in two steps.

Firstly, in a process known as arterial injection, blood is drained from the body and a chemical preservative is injected into the body to replace the blood. Normally, the drain from the embalming table is connected directly to the local sewer system and the blood and chemicals enter the sewage system.

Secondly, in a process known as aspiration, body fluids are removed from the hollow organs and replaced by a chemical preservative. Once again, the body fluids are drained into the local sewage system.

Various methods have been used for the aspiration of the hollow organs. In one, a hydroaspirator uses the water pressure from the local mains and a venturi valve to suck out the fluids from the hollow organs of the body. All of these fluids, including the excess water used for the aspiration process, which may amount to several tens of gallons, are flushed down the local drains. The embalmer uses a trocar to aspirate all the hollow organs, both thoracic and abdominal, and the resulting cavities are filled with cavity formalin.

In another process, infrequently used, an air pump is used to evacuate glass jars which in turn cause suction on a tube which is connected to the trocar and which trocar can be used to aspirate the hollow organs. The fluids from the hollow organs collect in the jars, and these jars are then emptied down the local drains. An example of one such air pump is the Sico No. 1025 Air Pump.

A significant problem with any of these methods is that they drain embalming chemicals and body fluids, including blood, into municipal sewage systems, and from there into the environment. The hydroaspirator also uses excessive amounts of water to create the necessary suction to remove body fluids from the hollow organs.

One proposed solution to the problem of disposing of body fluids has been on-site storage of the body fluids at the premises of undertakers. There are several objections to this solution. A person's blood is a body organ, and the solution results in the mingling of peoples' blood. In addition, on-site storage is expensive to maintain and clean, and the fluids must be disposed of eventually.

In addition, all of these methods suffer the disadvantage that any handling of body fluids after the removal of the body fluids from the body can result in contamination and the risk of exposure to disease.

SUMMARY OF INVENTION

The inventor has found a solution to the disposal of body fluids during the embalming process. The essential aspects of the invention are set out in the claims which form a part of this patent.

For example, in one embodiment, the invention provides a method for preparing a corpse for burial or cremation comprising: aspirating the hollow organs of the corpse with aspirating means to remove fluids from the hollow organs, collecting the removed fluids in a disposable container, and installing the disposable container in a coffin or casket that contains the corpse for burial or cremation.

In another aspect, the invention provides a disposable container having a first end and second end, and being shaped for insertion in a coffin, and having inlet means for insertion of fluids into the disposable container:
 the disposable container tapering towards the second end and having sufficient rigidity to withstand the suction required to aspirate hollow body organs, the disposable container having outlet means for evacuation of air from the disposable container and including valve means connected to the outlet means for preventing backwash of fluids into the outlet means from the interior of the disposable container; and
 means disposed within the disposable container to shield the outlet means from splashes caused by insertion of fluids into the container.

In another aspect the invention provides a corpse preparation device comprising a disposable container having a first end and second end, and being shaped for insertion in a coffin, and having inlet means for insertion of fluids into the disposable container; the disposable container tapering toward the second end; and the disposable container including a portion having a lower melting point than the remainder of the container.

In another aspect, the invention provides a system which incorporates the disposable container and further includes a vacuum pump connectable to the outlet means, and aspirating means connected to the inlet means.

BRIEF DESCRIPTION OF THE FIGURES

There will now be described preferred embodiments of the invention, with reference to the drawings by way of example, in which.

DETAILED DESCRIPTION OF THE PREFERRED EMBODIMENTS

The invention provides a disposable container, a system which incorporates the disposable container and a method of utilizing the disposable container for the disposal of body fluids.

SYSTEM

Figure 1:
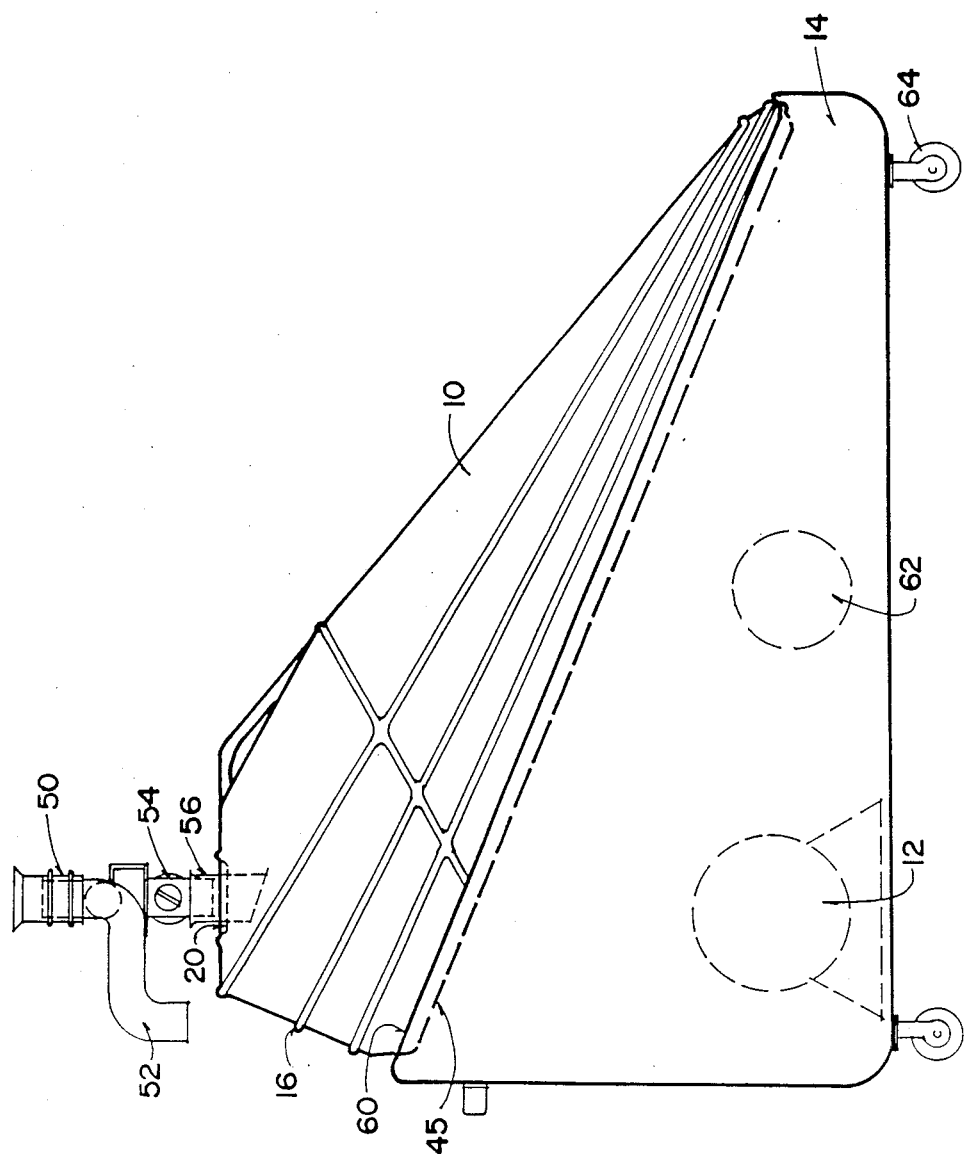
FIG. 1 is a side view of a system according to the invention including disposable container, trolley and two way valve.

A disposable container or specific reservoir 10 is shown in each of the FIGS. 1, 2, 3, 4, 5 and 6. As shown in the Figures, the disposable container is specially shaped to fit unobtrusively in a casket. Details of the disposable container 10 will be described later, but it has two main functions Firstly, as shown in FIG. 1, during arterial injection, blood from a body may be allowed directly into the disposable container 10 through valve 50. The valve 50 is connected to an embalming table, which is well known in the art (see FIG. 6), and fluids may flow from the gutter on the embalming table, through the tube 56 and into the disposable container 10. The disposable container 10 is oriented with its tapered end down, and its lower surface sloping downward, to help prevent splashes of blood out of the container during drainage of blood.

Secondly, the disposable container 10 is used during aspiration of body cavities as a vacuum reservoir for sucking fluids out of the body, and for containing the fluids.

Figure 6:
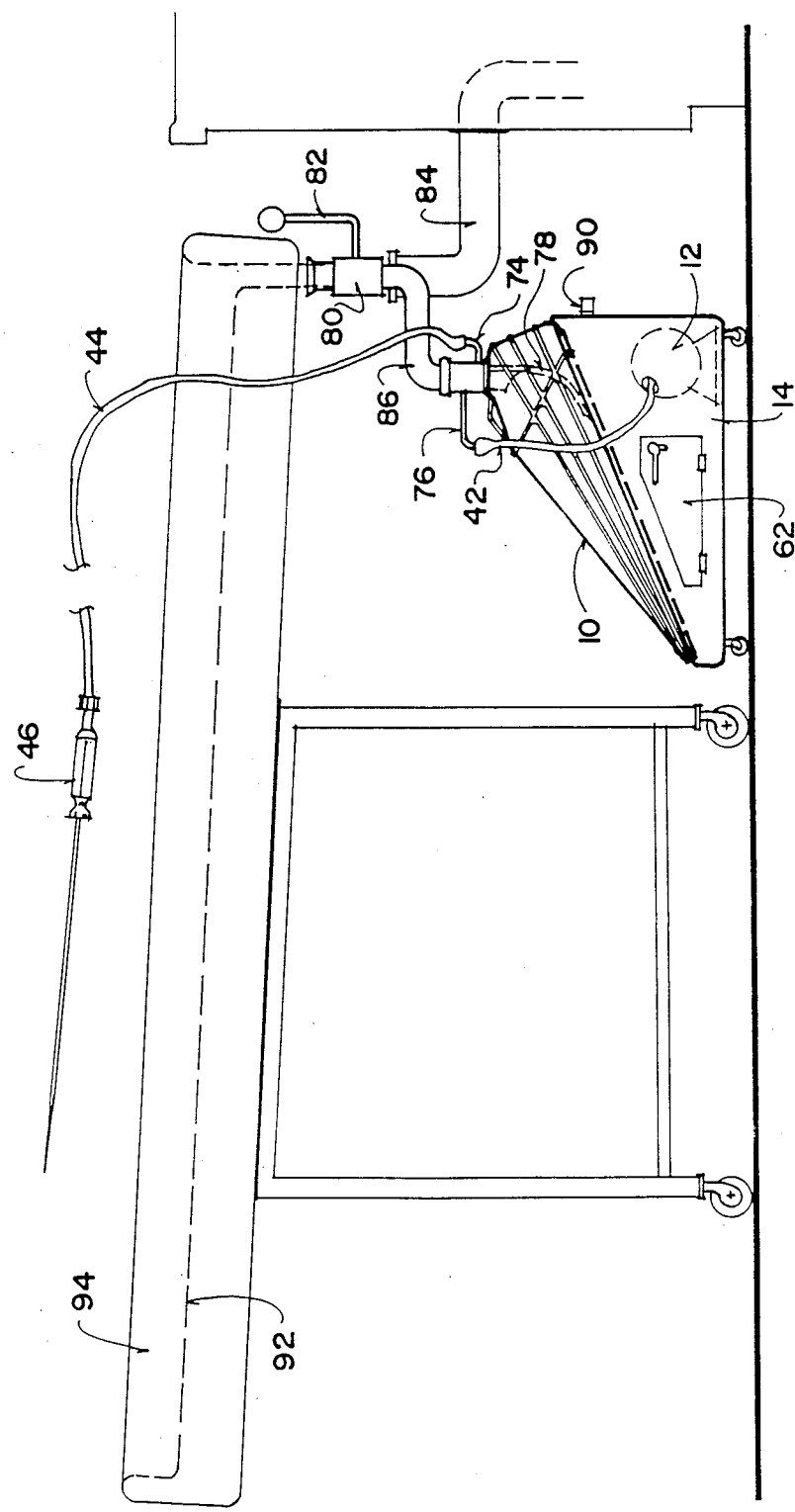
FIG. 6 is a side view of another system according to the invention.
Figure 7:
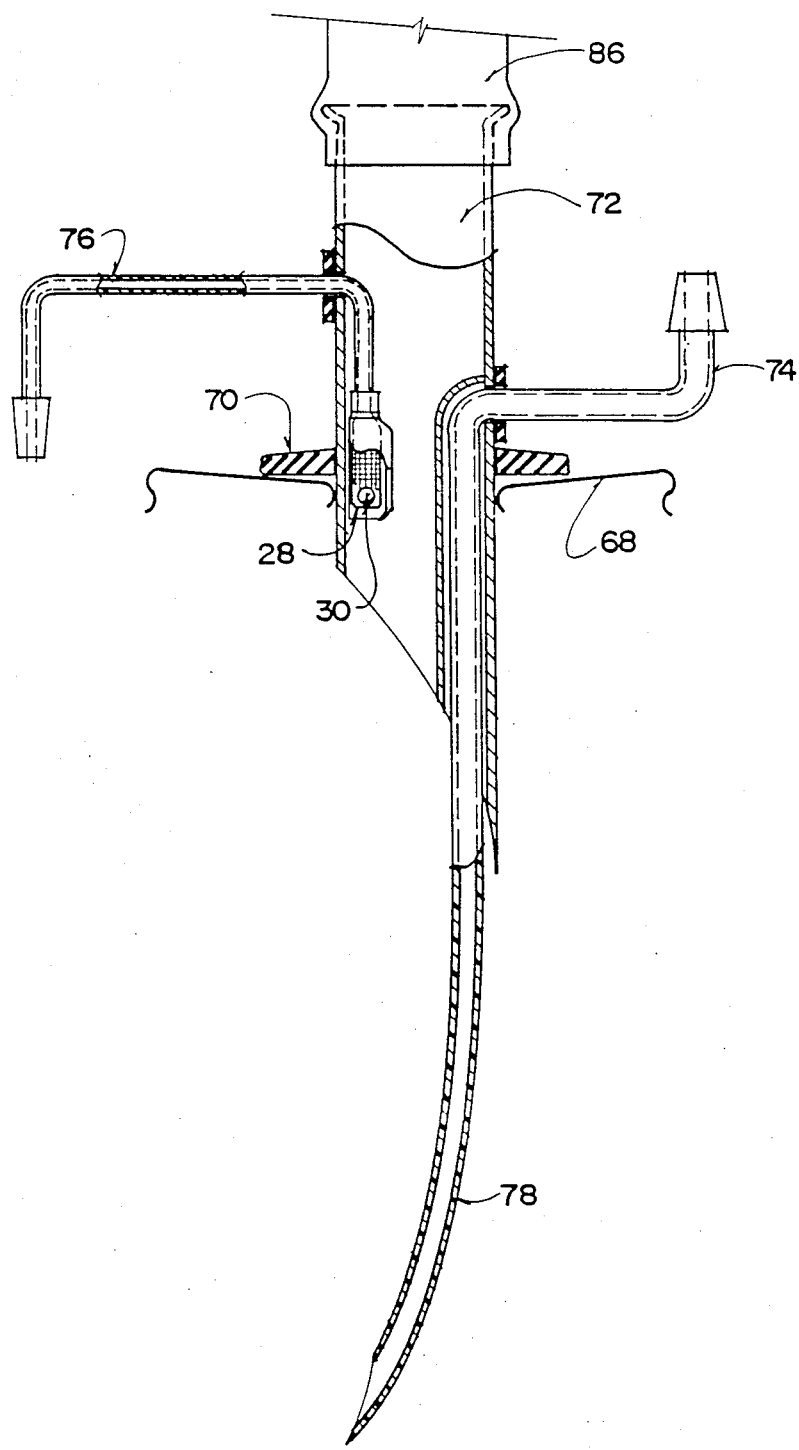
FIG. 7 is a side view of a puncture fitting for a disposable container according to the invention.

In FIGS. 1 and 6, is shown the disposable container 10, a vacuum pump 12 and a trolley or base 14 for the disposable container 10. In use, the vacuum pump 12 is connected directly to the disposable container 10, evacuates it and the resulting vacuum draws body fluids into the disposable container 10.

In an alternative configuration of this system, the disposable container 10 is connected to a rack attached to the embalming table

DISPOSABLE CONTAINER

The disposable container 10 is preferably made of thermoplastic, which provides the required rigidity for suction and allows for clean cremation. It may, however, also be made of other kinds of plastic or steel, but when used for aspiration must have sufficient strength to withhold the vacuum required to aspirate the internal body organs. Alternatively, the disposable container 10 could be made from an airtight fabric covering over a ribbed network, which could be collapsible to a desired volume.

Figure 5:
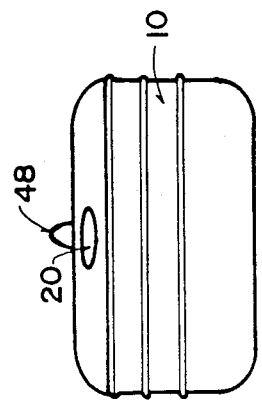
FIG. 5 is a front view of a disposable container according to the invention.
Figure 4:
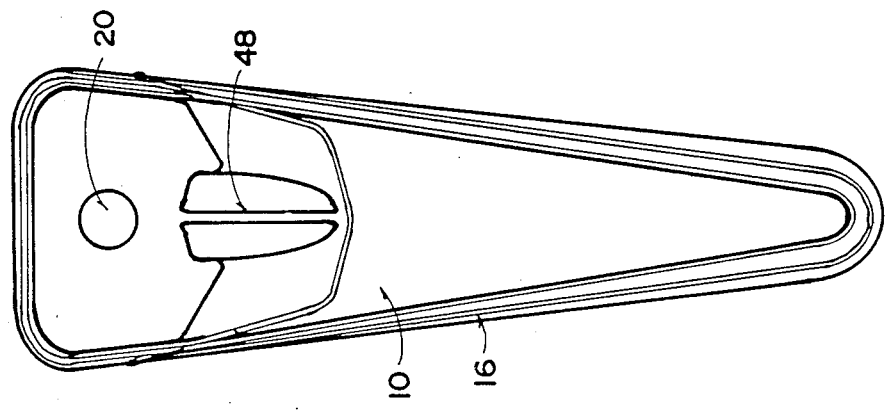
FIG. 4 is a top view of a disposable container according to the invention.
Figure 3:
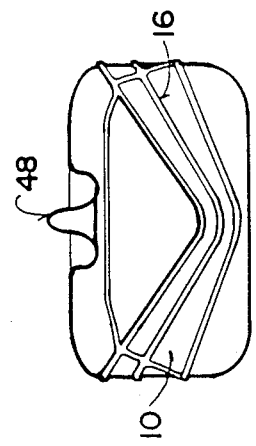
FIG. 3 is a rear view of a disposable container according to the invention.

The preferred shape of the disposable container 10 is an arrowhead or wedge shape as seen from both the top and side (see FIG. 4) for fitting between the legs and under the back of a corpse. As shown in FIGS. 3, 4, and 5, the disposable container 10 tapers from a first, wide end to a second, narrow end. The narrow end may be used to support the pelvis of a body for the proper orientation of the body for viewing.

The disposable container 10 may either be fitted between the legs of a body or may be used to support the head of the body. In either case, the pointed end of the disposable container 10 points toward the center of the casket.

A capacity of 1.5 to 3 United States gallons will typically be sufficient for holding body fluids of a person. The disposable container 10 is preferably ribbed with ribs 16 for additional structural strength.

Figure 2:
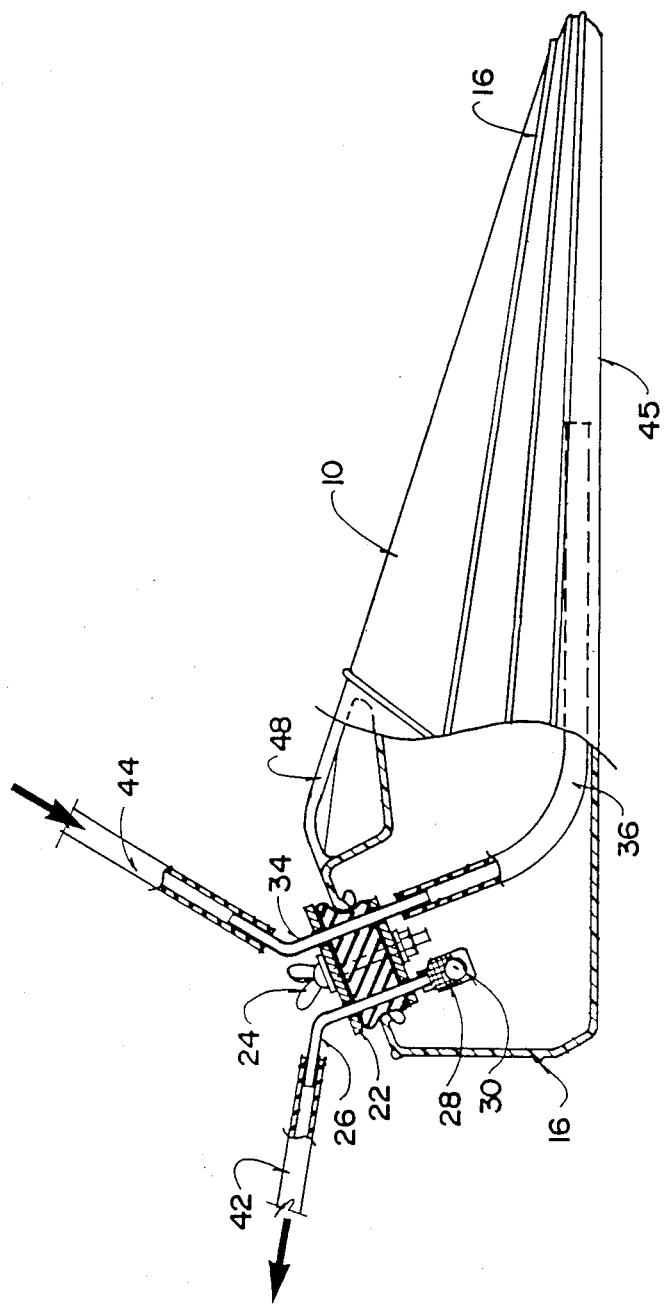
FIG. 2 is a cross-section through a disposable container according to the invention.

For use as a vacuum reservoir, the disposable container 10 must be airtight, while permitting it to be opened or pierced for insertion of blood during the process of arterial injection. To accomplish this, as shown in FIG. 2 for example, the disposable container 10 is provided with sealing means, for example a removable elastic bung, stopper or plug 22 made of rubber, which fits snuggly in the opening 20 in the first end of the container. The plug 22 is provided with a nut and bolt combination 24 or equivalent means for compressing the plug 22 to ensure a tight fit in the opening 20 of the disposable container 10.

The plug 22 is provided with two passage ways. One passage way receives a tube 26 to form an outlet for the evacuation of air from the disposable container 10. The interior end of the tube 26 is provided with a cage 28 and floating ball 30.

As fluids enter the disposable container 10, and fill the disposable container up, the floating ball 30 rises and shuts off the tube 26 so that no further air can be evacuated from the disposable container 10. This prevents contamination of the vacuum pump 12 with fluid.

The other passage way receives a tube 34 to provide an inlet means for insertion of body fluids into the disposable container 10. It is desirable to prevent backsplashing of body fluids towards the tube 26. Rubber sleeve 36 connected to the interior end of tube 34 has been provided for this purpose.

Air is evacuated from the disposable container 10 through tube 26 connected to air hose or tube 42, which in turn is connected to vacuum pump 12. Body fluids enter the disposable container 10 through tube 34 connected to hose or tube 44 connected directly to a trocar 46, (shown in FIG. 6 and well known in the art), which in turn may be used to pierce body organs and remove the fluids from them.

As shown in FIG. 1, the opening 20 and the surrounding surface of the disposable container 10 is oriented at an angle in relation to the lower surface 46 of the disposable container 10 such that, when the disposable container 10 is oriented in the preferred sloping position for insertion of body fluids, the opening 20 is horizontal and at the top of the disposable container 10.

The bung or plug 22 is preferably made of a material, such as rubber, that melts down before the material of the disposable container 10. In this way, during cremation, rupture or explosion of the disposable container 10 may be avoided.

An alternative to the use of a plug 22, is to use a puncturable self-sealing seal 68 as shown in FIG. 6.

The seal 68 is of such design as is commonly used in pharmaceutical applications. It forms a vacuum-tight seal for the disposable container 10. For the insertion of fluids into the disposable container 10, the seal 68 is pierced by a hollow needle 72 having attached to it, by any suitable means, inlet means 74 and outlet means 76. The inlet means 74 is connected to hose 44, which in turn is connected to trocar 46. The interior end of the outlet means 76 (on the inside of the hollow needle 72) is fitted with valve means comprising a cage 28 and floating ball 40 for preventing backwashing of fluids into the outlet means 76, and the exterior end of the outlet means 76 is connected by hose 42 to vacuum pump 12. The hollow needle 72 is also provided with a collar 70 to prevent over insertion of the hollow needle 72.

The inlet means 74 is preferably a semi-rigid or rigid tube, made for example of a suitable plastic, and has a pointed end 78 to assist in piercing the puncturable self-sealing seal 68. The end 78 is also preferably curved in such a way that it is tangential to the lower surface of the disposable container 10 at the tip of the end 78. In this way, fluid entering the disposable container 10 flows smoothly into the disposable container 10 without splashing. The inlet means 74 is attached to the hollow needle 72 so that it is on the inside of the hollow needle 72 below the collar 70, and passes through the hollow needle 72 just above the collar 70, to have its exterior end available for fitting on to the hose 74.

The outlet means 76 is also a tube made for example of a suitable plastic, and must be non-collapsible to withstand the suction created by the vacuum pump 12.

The disposable container 10 may be used on its own in conjunction with the bottle method of aspiration, with a loss of utility due to the additional hazard from splashes during transfer of body fluids from the bottles to the disposable container 10.

The disposable container 10 is also provided with a handle 48 located on a central upper portion of the disposable container 10, and may be pre-treated with a chemical preservative before insertion of body fluids.

Once insertion of fluids has been completed, the plug 22 may be replaced by a similar plug without passageways to seal the disposable container 10 during transportation of the disposable container 10 and emplacement in the casket.

BYPASS VALVE

Referring to FIG. 1, the bypass valve 50 is preferably attached to the lower end of the gutter on an embalming table. Both the gutter and embalming table are well known in the art and need not be described further here. Any suitable type of two-way valve may be used for the valve 50. The valve 50 is used to direct fluids from the gutter to either the local sewage system, for example for the disposal of water and soap used in washing a body, and to the disposable container 10 during arterial injection, so that blood and embalming fluid used in arterial injection is collected in the disposable container 10. As shown in FIG. 1, connection pipe 52 may be attached to a hose connected to the local sewage system and connection pipe 54 may be attached to a hose 56 which is inserted into the disposable container 10.

A second embodiment of a two-way valve is shown in FIG. 6. Valve 80, again any suitable type of two-way valve, is connected by a bracket (not shown) to the gutter 92 of an embalming table 94. The valve 80 is operated by lever 82. Lever 82 may select either the connection pipe 84 for the local sewage system or the connection pipe 86 to the hollow needle 72 inserted into the disposable container 10.

VACUUM PUMP

The vacuum pump 12 is preferably an air pump, for example, a Kinney Direct Drive Rotary Vane Vacuum Pump available from the Kinney Vacuum Company although any pump that provides the required suction may be used. The pump chosen should have sufficient power to evacuate the disposable container 10 and remove fluid from the hollow organs of a body. Instead of an air pump, a hydroaspirator could be used, with some loss of efficiency, by attaching the air tube of a hydroaspirator to the disposable container 10. The difficulty with using a hydroaspirator is that it uses large volumes of water. The vacuum pump 12 is connected to the disposable container 10 by air hose 42.

TROLLEY

A portable stand or trolley 14 may be used to support the disposable container 10 during insertion of fluids into the disposable container 10, and to transport the disposable container 10 from preparation room to casketting room. The trolley 14 is provided with a compartment for holding the vacuum pump 12 and a compartment 62 for holding fittings for the vacuum pump 12 and disposable container 10. The trolley 14 is provided with a sloping upper surface 60 to give the correct orientation to the disposable container 10 during insertion of body fluids.

Wheels or castors 64 are provided to permit easy movement of the trolley 14. As shown in FIG. 6, a clip 90 is provided for retaining the hose 42 leading to the vacuum pump 12.

The trolley 14 is preferably made of a hard plastic or steel or some other easy to clean material. Its upper surface 60 may be ridged to provide stability and ease of positioning of the disposable container 10.

METHOD OF OPERATION

The method of using this disposable container 10 and the system described here in the embalming process is as follows. A body is placed on the embalming table in the preparation room, and the drain bypass 50 or 80 is set so that cleaning fluids (for example, water and detergent) will drain into the local sewage system. The body is then disinfected in accordance with normal practice and body features are set and blood vessels raised.

Next, the disposable container 10 is placed on the trolley 14 and positioned so that the opening 20 is underneath the pipe 54 of valve 50 or connection 86 of valve 80. Valve 50 or 80 is then set so that fluids drain from the gutter of the embalming table into the disposable container 10.

In accordance with normal practice, one artery is incised, a canula is inserted into the artery for injection of arterial chemicals, and drainage instruments set for drainage of blood. Arterial chemicals are mixed and injected into the arterial system. During arterial injection, in accordance with the invention, blood and excess arterial injection chemicals are drained through the valve 50 or 80 into the disposable container 10. When injecting is finished, the table is rinsed with a minimum amount of water.

The valve 50 or 80 is again set so that fluids from the embalming table go to the local sewage system. The vacuum fitting or plug 22 is inserted in the opening 20. The hose 44 is connected to the tube 34 in the plug 22. The vacuum pump 12 is turned on.

Next, an incision is made for the trocar 46, and the trocar 46 used to aspirate the thoracic and then the abdominal cavities. Fluid from these cavities is sucked into disposable container 10 through hose 44.

Once aspiration is finished, the disposable container 10 may be topped off with arterial chemical to prevent further contagion in the disposable container 10. The vacuum pump 12 may be turned off, and the hose 44 removed from the disposable container 10. The hose 42 leading to the vacuum pump 12 may be removed and stored on the trolley 14.

Next, a hermetically sealing plug is installed on the disposable container 10 to prevent fluids leaving the disposable container 10. In accordance with normal practice, incisions are next sutured, and with the valve 50 leading to the local sewage system, the body is washed, dried, dressed and cosmetics applied.

The disposable container 10 is taken to the casketting area, and the bedding of the casket adjusted to accommodate and conceal the disposable container 10. The disposable container 10 is placed in the casket. If one disposable container 10 is used, it is placed between the legs within the bedding of the casket, with the large end toward the foot end of the casket. If two disposable containers 10 are used, the other may be inserted under the casket pillow with the small end of the disposable container 10 under the upper back. Finally, adjustments may be made for the elevation of the head and other orientations of the body.

In an alternative embodiment, during arterial injection, fluids may be diverted directly to the disposable container 10 through a length of tubing attached directly to the carotid, femoral or axillary veins. If this method is used, the valve 50 or 80 may continue to route excess water, used for example during massage, to the local sewage system.

In addition, while a specially shaped bag or other flexible container could be used in association with a bottle aspirator (in which the bottle is evacuated by an air pump, the bottle vacuum is used for aspiration and the contents of the bottle are emptied into the bag or flexible container), such a bag or other flexible container would be awkward to use and handle, and may result in undesirable splashing of body fluid.

Immaterial modifications to the invention may be conceived by persons skilled in the art, but these are intended to be covered by the claims that follow.

I claim:

1. A corpse preparation device comprising:
a disposable container having a first end and second end, and being shaped for insertion in a coffin, and having inlet means for insertion of fluids into the disposable container:
the disposable container tapering towards the second end and having sufficient rigidity to withstand the suction required to aspirate hollow body organs, the disposable container having outlet means for evacuation of air from the disposable container and including valve means connected to the outlet means for preventing backwash of fluids into the outlet means from the interior of the disposable container; and
means disposed within the disposable container to shield the outlet means from splashes caused by insertion of fluids into the container.

2. The corpse preparation device of claim 1 further including an opening in the first end of the disposable container, and means for sealing the opening.

3. The corpse preparation device of claim 2 in which the outlet means and inlet means are disposed in the sealing means, and the valve means includes a cage attached to the interior end of the outlet means and a floating ball contained within the cage.

4. The corpse preparation device of claim 2 in which the sealing means is a puncturable seal.

5. The corpse preparation device of claim 1 in combination with an air pump connectable to the outlet means and aspirating means connected to the inlet means.

6. The corpse preparation device of claim 1 in combination with an air pump connectable to the outlet means and aspirating means connected to the inlet means and further including an opening in the disposable container, and means disposed in the opening for sealing the disposable container.

7. A corpse preparation device comprising:
a disposable container having a first end and second end, and being shaped for insertion in a coffin, and having inlet means for insertion of fluids into the disposable container;
the disposable container tapering toward the second end; and including a portion having a lower melting point than the remainder of the container.

8. A corpse preparation system comprising:
a disposable container having a first end and second end, and being shaped for insertion in a coffin, and having inlet means for insertion of fluids into the disposable container, the disposable container tapering toward the second end, having sufficient rigidity to withstand the suction required to aspirate hollow body organs and having outlet means for evacuation of air from the disposable container and including valve means connected to the outlet means for preventing backwash of fluids into the outlet means from the interior of the disposable container;
in combination with an air pump connectable to the outlet means and aspirating means connected to the inlet means; and
the outlet means and inlet means being disposed in the sealing means, the valve means including a cage attached to the interior end of the outlet means and a floating ball contained within the cage.

9. The corpse preparation system of claim 8 further including a two-way valve connectable to the gutter of an embalming table, and having first and second connectors, the first connector being connectable to a drain and the second connector being connectable to the disposable container.

10. The corpse preparation system of claim 8 further including a trolley for supporting the disposable container.

11. The corpse preparation system of claim 10 in which the disposable container has a lower surface connecting the first and second ends, the trolley has a base, the surface of the disposable container adjacent the opening being oriented at a first angle of less than 90 degrees to the lower surface, and the trolley having a top surface oriented at the first angle with respect to the base of the trolley.

12. The corpse preparation system of claim 8 in which the disposable container has a lower surface connecting the first and second ends, the surface of the disposable container adjacent the opening being oriented at an angle of less than 90 degrees to the lower surface.

13. A method of preparing a corpse for burial or cremation comprising:
aspirating the hollow organs of the corpse with aspirating means to remove fluids from the hollow organs;
collecting the removed fluids in a disposable container; and
installing the disposable container in a coffin or casket that contains the corpse for burial or cremation.

14. The method of claim 13 further including installing the disposable container between the legs of the corpse.

15. The method of claim 13 in which aspirating the hollow organs of the corpse includes evacuating the disposable container using an air pump, and sucking fluids from the body using the vacuum created in the disposable container.

16. The method of claim 13 in which the method comprises, before aspirating the hollow organs of the corpse, draining blood from the body and collecting the blood in the disposable container.

* * * * *